United States Patent [19]

Sklar et al.

[11] Patent Number: 5,054,907
[45] Date of Patent: Oct. 8, 1991

[54] OPHTHALMIC DIAGNOSTIC APPARATUS AND METHOD

[75] Inventors: H. Alfred Sklar, San Francisco; Alan M. Frank; Charles McMillan, both of Livermore, all of Calif.; Olga M. Ferrer, Miami, Fla.

[73] Assignee: Phoenix Laser Systems, Inc., San Francisco, Calif.

[21] Appl. No.: 456,109

[22] Filed: Dec. 22, 1989

[51] Int. Cl.$^5$ .............................................. A61B 3/10
[52] U.S. Cl. .................................... 351/212; 351/247
[58] Field of Search ................. 351/212, 247; 356/376

[56] References Cited

U.S. PATENT DOCUMENTS 4,312,574  1/1982  Wilms ................................. 351/212
4,878,750  11/1989  Sekiguchi ........................... 351/212

OTHER PUBLICATIONS

S. G. El Hage, "Suggested New Methods for Photokeratoscopy, A Comparison of their Validities, Part I", *American Journal of Optometry and Archives of American Academy of Optometry*, pp. 897–912, 11/71.

*Primary Examiner*—Rodney B. Bovernick
*Attorney, Agent, or Firm*—Thomas M. Freiburger

[57] ABSTRACT

An ophthalmic diagnostic instrument determines the shape of the cornea through projection of an image onto the cornea through the optics of the diagnostic instrument. The instrument and the method of the invention involve folding a projected pattern of discrete separated point light sources so that the pattern is projected toward the eye coaxially with return collected light reflected off the cornea. The instrument avoids any need for a pattern light source directly adjacent to the eye, and provides the surgeon or other eye care specialist with a real time image accurately displaying the shape of the cornea. The surgeon is thus able to monitor the corneal shape prior to surgery, to monitor its changes during the course of the surgery, and to further monitor the cornea in post operative stages. In a specific embodiment of the invention, a real image of the pattern of point light sources is formed inside or very closely in front of the objective lens of the system so that the objective lens becomes a field lens and the angle of view of the system is enlarged.

30 Claims, 8 Drawing Sheets

| CORNEA ANTERIOR SURFACE | 2 o'clock | 1 o'clock | 12 o'clock | 11 o'clock | 10 o'clock |
|---|---|---|---|---|---|
| K-Reading → V | 41.8 | 43.5 | 44.0 | 43 | 42 |
| Thickness → V | .575 | .528 | .505 | .530 | .570 |
| K-Reading → H | 39 | 42 | 44.0 | 41 | 40 |
| Thickness → H | .580 | .535 | .505 | .538 | .560 |

OPHTHALMIC DIAGNOSTIC APPARATUS AND METHOD

BACKGROUND OF THE INVENTION

This invention relates to ophthalmic analytical and diagnostic systems, and in particular the invention is concerned with obtaining accurate determinations of the shape of the human eye structures such as the cornea, the lens and the retina. An apparatus in accordance with the invention measures, calculates and displays the shape of selected cross sections of the cornea, for example, and is intended for use by ophthalmic surgeons as well as the eye care community at large.

One of the principal activities of the eye care specialist, which includes both ophthalmologists and optometrists, is to determine the refractive power of the eye as an optical system. Since the only major refractive index change along a light path entering the eye to impinge on the retina occurs on the first air to tear layer interface or, approximately, at the corneal anterior epithelial surface, the precise measurement of the shape of the corneal epithelial surface is the key to estimating the refractive power of a given eye.

Traditionally, the eye care specialist has been satisfied with a measurement from keratometric readings. The keratometric readings ("K-readings") correspond to the curvature of the corneal epithelial surface at the intersection of the corneal epithelial surface with the central visual axis of the eye. The K-readings are usually displayed in diopter power which is proportional to the reciprocal of the radius of curvature. The K-readings provided by keratometers correspond to the curvatures at one point on the corneal epithelial surfaces along two surface rays passing through that point. Usually, the two rays match the semi-major and semi-minor axes of the eye which are the nasal-temporal (horizontal) axis and the superior-inferior (vertical) axis of the eye.

Since the first concern of the eye care specialist is central, axial vision, the K-readings, which only provide two curvature measurements along the semi-major and semi-minor axis normal to the visual axis, represent a fair estimate of refractive power along the most critical light paths in the human eye.

To date, the eye care community has relied on the eye surface being approximated as a combination of a sphere and a cylinder, thus the reference to 20/20 as a visual standard. This approximation is exact at the intersection of the corneal anterior surface with the visual axis. The approximation is known to fail as one proceeds radially outward from the central visual axis towards the limbus, roughly the outermost edge of the cornea where the triple-point transitions between cornea, sclera, and iris tissues take place.

There are several instruments for measuring the location of the corneal anterior surface in proximity of the limbus as well as in the central region, but the display generated from these measurements usually assumes that the eye can also be approximated as a combination of spheres and cylinders. In a sense, these instruments spread the error in approximating the shape of the corneal surface from being concentrated toward the limbus to being distributed over a greater region.

Notable exceptions are instruments based on confocal microscopy that measure the actual curvatures without simplifying assumptions. However, systems based on confocal microscopy have very limited fields of view, considerably smaller than the full corneal surface. Such systems must then rely on a sequence of measurements over time which are subsequently made to piece together using either fractal techniques or some boundary matching algorithm. These paste-ups involve some form of interpolation, albeit on the boundary of the images rather than in the interior. In contrast with interpolations which are based on a sparse set of measurements, confocal techniques provide dense measurements at the expense of not having them performed simultaneously. Even though the sequential measurements can be formed very quickly, involuntary eye motion is known to occur within millisecond time scales, faster than the time required to complete data gathering using confocal techniques. This can introduce errors.

Since only a finite number of measurements of the actual location of the corneal anterior surface are possible, interpolation techniques are an intrinsic part of displaying a continuous shape based on the measured information. In most instruments still in use by the eye care community, the error in measuring the shape of the corneal anterior surface is often not in the measurement technique but in the numerical interpolation techniques utilized to prepare the display of the continuous corneal surface cross-section.

SUMMARY OF THE INVENTION

In accordance with the present invention, a system, apparatus and method for corneal shape determination and other eye structures achieves a high degree of accuracy by real-time measurements, calculations and display.

An interpolation technique used in accordance with the invention is based upon not only measuring the location of a given set of points on the surface of the corneal tear layer, but in performing the measurement in such a manner as to be able to solve the non-linear ordinary differential equation describing the surface in real time. This technique further provides several higher order derivatives which are used in generating the continuous corneal shape.

Aside from improving the K-readings while simultaneously reducing the global error in approximating the shape of the cornea's anterior surface, the process and apparatus of this invention are designed to provide the actual corneal shape in real time. By real time is meant faster than an eye care practitioner's capacity to observe and recognize a change in corneal shape, generally on the order of one second or less.

Several instruments have claimed capability of measuring a corneal cross-section shape in real time, as defined herein. These have relied on a combination of scanning techniques, confocal microscopy techniques, and image reconstruction techniques. Namely, using confocal microscopy, a high-resolution set of measurements is taken of selected small segments of the corneal cross section and the shape of the individual crosssection pieces is analyzed and then fitted together with the other separately scanned shapes to provide an approximating shape.

Given that the human eye is constantly in motion either through voluntary or involuntary actions and that these motions do not necessarily correspond to rigid body motions, scanning techniques which later patch up different pieces of the corneal cross section may have errors introduced by eye motions and eye distortions. The errors may be diminished by utilizing high-speed scanners, but are not removed.

The advantage of the described scanning technique is that it allows for performing a high number of measurements in a small region, thus generating very high resolution and accurate definition of the shapes in the limited area observed. To achieve the same resolution globally, that is from limbus to limbus, would require an unwieldy instrument with many light sources and measurement points. Hence speed is achieved with the scanning technique as well as high local resolution at the expense of global uncertainty due to the patchwork effort.

In one of the embodiments of the present invention, the instrument achieves comparable high local resolution without risking the uncertainty of global accuracy. This is achieved by performing a global measurement whereby the field of view of the instrument is adjustable. Thus, when global information is desired as to the shape of the cornea, one measurement rather than a sequence of scans is performed. And when a high resolution measurement is required of a particular region of the corneal surface, one of the embodiments of the invention will be able to narrow the same number of measurements into a limited field surrounding the desired corneal region.

The approach is comparable to the use of photolithography to generate pattern cuts in the semiconductor industry in the sense that a large template is progressively focused into smaller regions to generate tighter and smaller effects. In preferred embodiments of the present invention a zooming technique is used to define the field of view, and a corresponding zooming technique is used to enlarge the field to fill the display monitor.

One of the important considerations to ophthalmologists seeking to perform corneal reconstructive surgery, whether by radial keratotomy, corneal epikeratoplasty, keratimileusis, keratophakia, wide area laser ablation, or other procedures, is to accurately and reliably measure the shape of the cornea. This is important not only prior to the initiation of a surgical procedure, but also during evolution of the shape in the surgical procedure, and after the surgery, as the healing process takes over postoperatively.

One of the features of the present invention is not only to satisfy the corneal global measurement needs of pre- and postoperative surgical procedures, but to likewise provide the high resolution needed to follow the effects of surgery during the course of the procedure. For example, to determine the depth of an incision during a radial keratotomy procedure, the surgeon preselects the depth of the protruding diamond blade from the scalpel and depresses the full depth of the blade into the cornea. Surgeons are therefore relying that a uniform thrust pressure on the blade point can be maintained as the scalpel is traversed over the cornea and that the shape of the cornea does not deform during the course of the procedure. It has been often observed that the cornea deforms during the course of radial keratotomy. Thus, the surgeon is left guessing and relying on his own intuition as to the incision depth of radial cuts. The depth of the incisions becomes progressively uncertain with each successive cut because of the increased deformation.

In one of the embodiments of the invention, the surgeon is enabled to first determine the corneal shape immediately prior to commencing the procedure, then to observe the measured incision depth of each cut as it is being performed, to readjust his blade progressively as needed based upon actual incision depth measurement, and then once again to provide a global measurement of the resulting corneal shape.

Another problem addressed by the present invention again involves the utility of a measurement device during surgery. Keratometers have currently been used in surgical theaters, such as the Terry keratometer, but their efficacy has been limited not only by the extent of the information provided, but by their accuracy and by the obstruction of the patient's eye to the surgeon while the measurement is being performed. One of the reasons for this obstruction is mandated by the need to provide a field of illuminated points which the keratometer then detects as reflections from the cornea.

In order to get reflections or data points near the central visual axis, keratometers have needed to place such illumination points near the central visual axis. These illuminators are bulky and get in the way of the surgeon's access to the eye on which he is operating. In one of the embodiments of the present invention, this problem is solved by placing the illuminators a considerable distance away from the eye, folding an image of the illuminators into either a surgical microscope or other imaging apparatus via a beam splitter, and then rather than physically placing the illuminators along the visual axis, the present invention projects a real image of the illumination points at the location where the illuminators would have been required. This location is between the patient's eye and an objective lens of the instrument, or of a surgical microscope to which the instrument is attached. The real image is reflected off the surface or surfaces of interest in the eye, and reflected illumination points parallel to the optical axis of the instrument are collected and detected through the instrument. A real-time display is generated, preferably with ocular cross sections as selected by the surgeon, along with numerical topological data.

An important aspect of the present invention is that the optics of the system use the objective lens as a field lens for the pattern image and that the optics relay the Fourier plane of the objective lens, located behind the objective lens in the system, to a relayed, distant position in the instrument. This gives the opportunity and the spatial distance to fold in one or two light source patterns, between the Fourier plane of the objective lens and the relayed or transferred position of the Fourier plane. In one embodiment, as discussed below, two different light source patterns may be folded into the optical axis of the instrument, using two different beam splitters.

In this regard, two separate displays can be formed for real time review by the surgeon. One, a qualitative image showing elevation contours of the eye, derived from a series of concentric light rings; and the other from a selected pattern of discrete points of light, for quantitative analysis in producing cross sectional representations of the shape of the cornea.

The utility of the invention is not restricted to improving radial keratotomy procedures. Any surgical procedure which seeks to alter the refractive power of the eye benefits from having accurate displays showing the course and effect of the procedure. More generally, any surgical procedure which invades the eye and which in turn necessitates wound closure can be greatly benefited by the process and apparatus of the invention. Also, the instrument can be used for purely diagnostic purposes, such as by an optometrist for fitting contact lenses.

The various embodiments described correspond to different configurations depending on the actual needs of the surgeon. The common feature is to provide high resolution wherever it is mandated while preserving computational speed and global accuracy wherever extreme resolution can be relaxed.

It is therefore among the objects of the invention to enhance ophthalmic diagnostic and surgical procedures by providing an apparatus, system and method for high speed, real time precision monitoring of the shape of the cornea, both epithelial and endothelial surfaces, and of other ocular surfaces. These and other objects, advantages and features of the invention will be apparent from the following description of preferred embodiments, considered along with the accompanying drawings.

DESCRIPTION OF THE PREFERRED EMBODIMENTS

Figure 1:
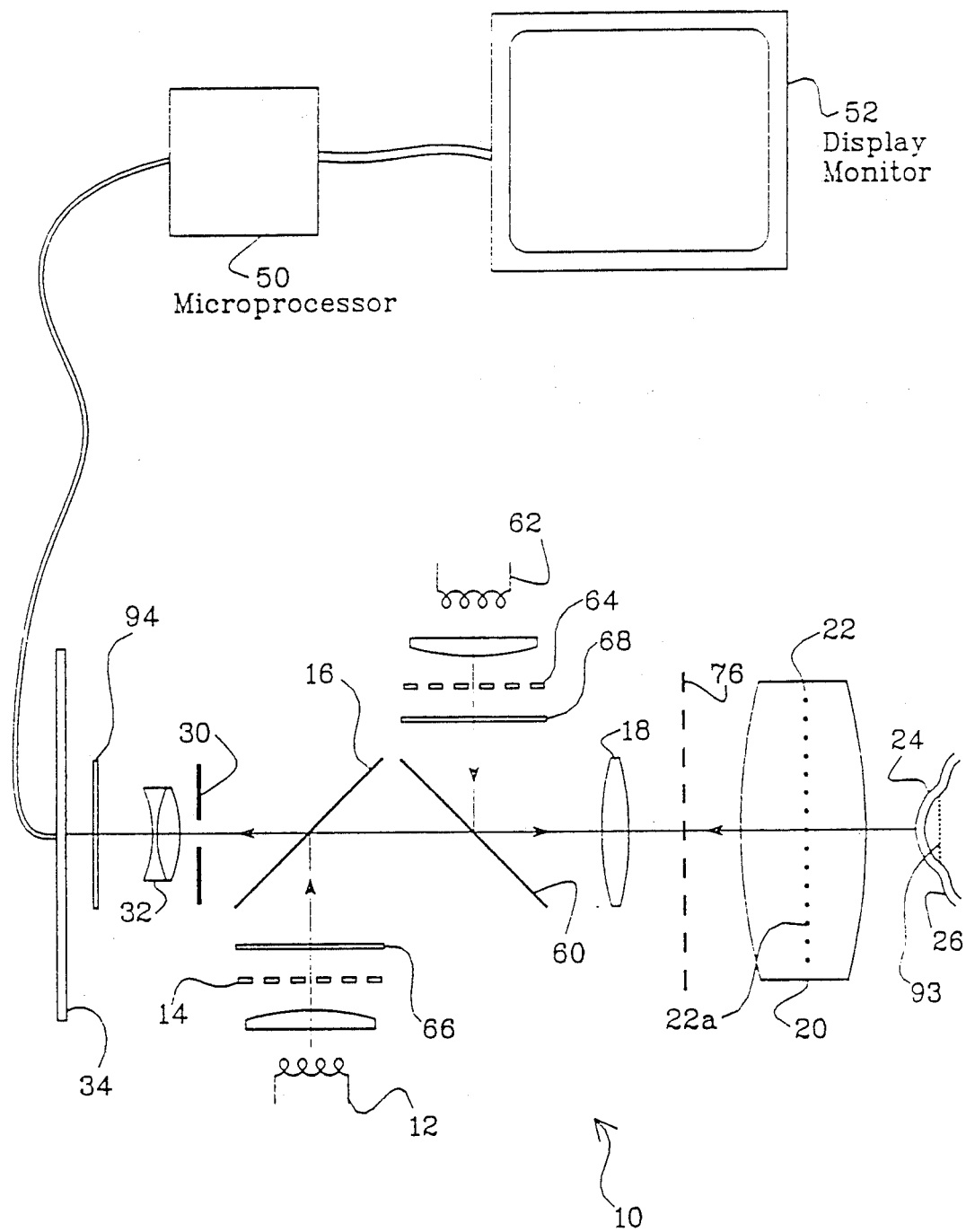
FIG. 1 is a schematic diagram showing the layout of an ocular diagnostic system and apparatus in accordance with a preferred embodiment of the present invention. The figure shows a series of optical elements which can be incorporated in this embodiment of the invention.

In the drawings, FIG. 1 shows in schematic representation a system of optical elements in accordance with the invention for use in carrying out ophthalmic diagnosis and analysis.

The system, generally identified by the reference number 10, includes an illuminator or light source 12, a pattern plate or disk 14 having a pattern of holes cut in the plate for producing a desired pattern of discrete light sources, a non-distorting beam splitter 16, a lens 18 which projects an image of target 14 onto an image plane at 22. This image plane 22 is close to or coincidental with the system of objective lens 20. The purpose of placing the image at this location 22 is to have the objective lens 20 serve as a field lens, that is bending the rays of light that form the image towards the patient's cornea 24.

As indicated in FIG. 1, the focused image 22 of the pattern is a real image, formed at some plane at or near the lens 20 and between the lens and the patient. The real image preferably is in the lens 20, but it can be very closely in front of the lens (i.e. a few millimeters in front). In this real image, each point source of light 22a projects a cone of light toward the patient. Thus, each point source 22a in the real image makes an infinite number of specular reflections off the front surface of the cornea 24 of a patient's eye 26. As explained below, the F-number of the final lens 20 determines the maximum area of the cornea that can be measured. The objective lens serves as a field lens, and the patient's cornea must be at the focal length of the lens 20. This assures that the light reflected off the eye parallel to the optical axis of the instrument is then brought to a point behind the lens 20 at the focal distance of the lens 20. This enables the return light to be apertured down as discussed below, to select only those rays which were paraxial off the eye. This enables the system to localize a detected point to a point on the cornea from which that ray was reflected. If the objective lens 20 were not situated to serve as a field lens, outermost points of light in the pattern would not reflect off the cornea. As a field lens, the lens 20 efficiently bends the outer points of light toward the eye.

It is preferred that the focal length of the lens be great enough to provide an unobstructed, comfortable distance from the instrument to the patient and adequate working room for the surgeon, for surgical applications.

The F-number of the objective lens 20 is most important in its function as a field lens as it will determine the maximum angle from the optical axis at which a ray can be reflected from the cornea parallel to the axis. If for example a commercially available F/2 lens is used, then the region of coverage will be about 3 mm diameter on the cornea. A lens with a smaller F-number will cover a proportionally larger region on the cornea.

Figure 1A:
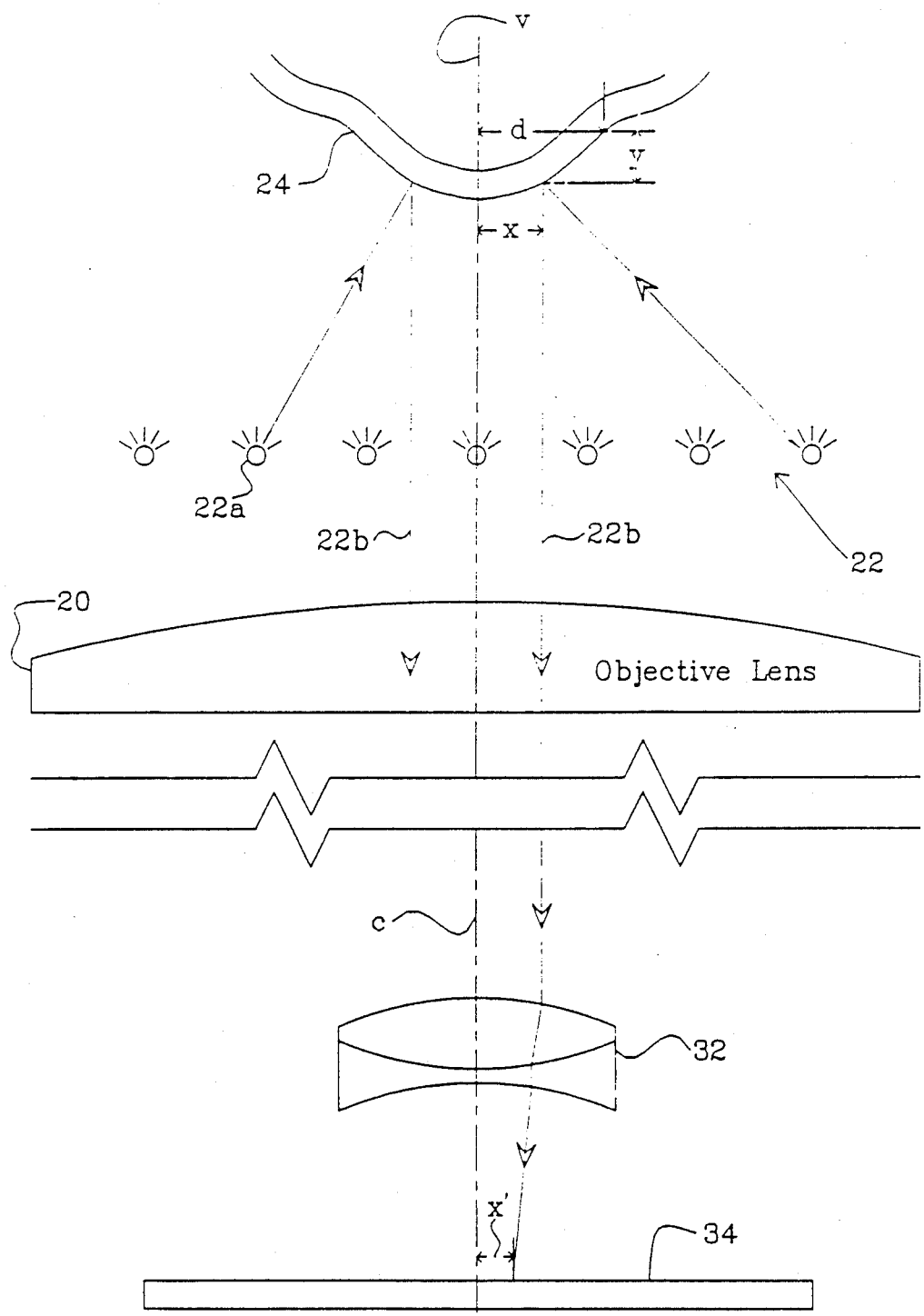
FIG. 1A is a schematic diagram showing in greater detail certain portions of the system of FIG. 1.

As indicated in FIG. 1A, each of the real-image point light sources 22a makes at least one reflection 22b which will be parallel to the central axis of the objective lens 20, with all axial reflected rays 22b parallel as shown in the drawing. For each point light source 22a, the reflected axial ray 22b will be unique unless the corneal surface has extremely strong local imperfections or distortions in the corneal curvature, which could theoretically cause more than one reflected axial ray 22b to occur, from spaced locations on the cornea.

Other rays of light reflected off the cornea will reach and pass through the lens 20, but as will be seen below, only those returning reflected rays which are very nearly parallel are passed through the system for analysis. Those are the rays and points which will supply data points to be compared with the original pattern as projected through the plate 14 to supply data which can be solved to determine the shape of the cornea.

As shown in the overall schematic view of FIG. 1, the returning reflected rays pass back through the lens 20, then through the lens 18 and the beam splitter 16, an aperture or spatial filter 30 and a further lens 32, ultimately to be focused on a detector or camera plane 34.

The curvature of the cornea 24 forms a virtual image 93 of the target image 22. In the article "Suggested New Methods for Photokeratoscopy, a Comparison for Their Validities, Part I", by S. G. El Hage, *American Journal of Optometry and Archives of American Academy of Optometry*, November 1971, El Hage pointed out that an aperture or spatial filter at the back focal plane or Fourier plane of the objective lens 20 will only pass rays parallel to the axis thus localizing those rays from a given point of the virtual image 93 to those that are reflected from a specific point on the cornea 24. In this embodiment, it is desired to have space behind the objective lens 20, the lens 18 is used to relay the Fourier plane of the lens 20 to the aperture 30. The aperture 30, being in an image of the Fourier plane, will likewise select only those rays reflected from the cornea 24 parallel to the axis.

The rear lens 32 of the system focuses a distorted image of the virtual image 93 of point light reflections on the detector or camera plane 34.

As shown schematically in FIG. 1A, the camera plane 34 has a central axis c which lies on the optical axis of the system, including the objective lens. Ideally this axis is placed as closely as possible to the center of the cornea or visual axis v. If these axes are significantly displaced, then much of the light reflecting off the cornea will not be returned through the system. This discussion assumes the axes coincide, but adequate information can be obtained over small deviations (e.g. one millimeter). If a reflected, returned point lies on the center axis c of the camera plane 34, then that ray emanated from the visual axis v of the cornea, at least as respects one orthogonal direction on the cornea and on the camera plane 34, which is shown as the left-right direction in the plane of the paper in FIG. 1A.

Likewise, if a particular point of light is focused on to the camera plane or detector face 34 at a distance $x'$ from the center axis c, that distance corresponds to, and is linearly proportional to, a distance x of the reflecting point on the cornea for that ray 22b as measured from the visual axis v. If a depth distance y is determined, measured from an arbitrarily chosen datum d to the point of reflection on the cornea, and a series of such x and y can be determined, then a differential equation can be solved to define y as a function of x, giving the curvature of the cornea in this direction or along the subject axis, i.e. in the plane of FIG. 1A. Similarly, measurements and calculations can be made along an orthogonal axis on the cornea (e.g. the nasal-temporal and superior-inferior axes can be used), giving as much information regarding the cornea's shape as is normally needed for any diagnostic or surgical procedure.

The y distance indicated in FIG. 1A can be derived through information regarding the degree of distortion of the reflected point light pattern, and the spatial relationship among the points of light, as compared to the pattern as originally projected and as arranged in the real image 22. Thus, considering the parallel ray 22b in FIG. 1A, which is shown as emanating from the real image point light source 22a on the right in FIG. 1A, if the cornea curvature is less steep at the point of reflection, i.e. at a shallower angle with respect to a tangent to the cornea at the visual axis, then the parallel ray 22b would have originated from a different real image point source, one farther to the left in the pattern. The right-end point source 22a would have created a parallel reflection only from another point on the cornea, farther to the right as viewed in FIG. 1A. Each of the reflected points as detected at the camera plane 34 can be identified electronically, essentially by counting points in the array.

Figure 6:
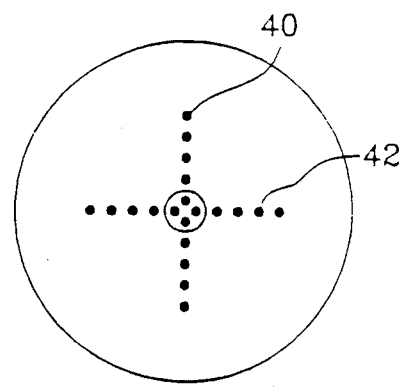
FIG. 6 is a schematic view showing a simple pattern of rectilinear sequences of point light sources which can be used for measuring the cornea in accordance with one embodiment of the invention.

FIG. 6 shows one example of a projected light pattern which can be used in the system and method of the invention. In this simple pattern, a vertical rectilinear array 40 is crossed orthogonally with a horizontal rectilinear array 42, with the intersection point corresponding to the visual axis of the eye. This is the simple pattern assumed with reference to FIG. 1A.

Figure 9:
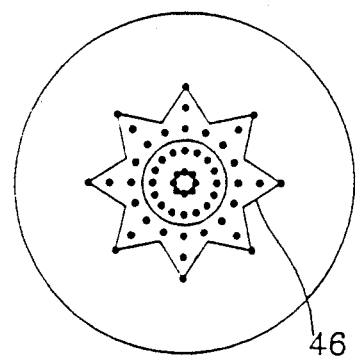
FIG. 9 is a schematic view showing a distortion of the pattern shown in FIG. 7, as an example of what may be read and analyzed by the apparatus of the invention for determining cornea shape.
Figure 7:
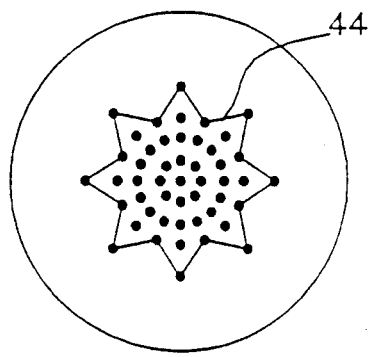
FIG. 7 is a schematic view similar to FIG. 6, showing another pattern which can be used for measuring the cornea.
Figure 10:
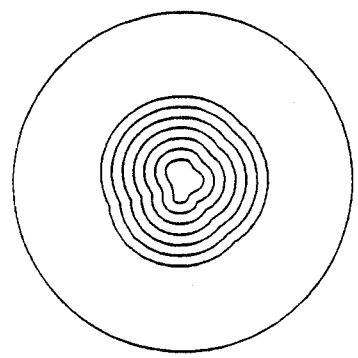
FIG. 10 is another schematic view, showing a reflected pattern as produced by the projection shown in FIG. 8, and the distortion of the reflected pattern.

A more complex pattern 44 of points is shown in FIG. 7. This pattern, shown as an asterisk-like pattern of linear arrays of points, gives data from many more points on the cornea. It may define an outline of a five-pointed star or any similar type of pattern, but preferably it has some means of identifying its rotational orientation. It may have an outline of a star with an odd number of points, so that the asymmetry can help identify the detected, reflected points by correlating them with the originally projected pattern 44. FIG. 9 shows an example of a reflected pattern 46 which might result from the pattern 44 shown in FIG. 7, as reflected from a cornea with some degree of distortion.

FIG. 1 schematically indicates that the detector or camera plane 34 is connected to a microprocessor 50. The microprocessor may be connected to a display device, such as a CRT monitor 52 as indicated. Data gathered from the system as described is received by the microprocessor 50 and analyzed. Each detected point is correlated with the location of the particular point in the source pattern from which it emanated. The x value is determined for each point, i.e. the distance from the optical axis v from which the point was reflected off the cornea. This is determined by direct proportioning, from the known magnification of the system. Each reflected point has an x value which is the distance from the optical axis of the system. Each linear array of points in the image must be separately analyzed and fitted to the mathematical approximation. If the complex pattern 44 shown in FIG. 7 is used, formed of an asterisk-like array, the analysis and computation are made along each line of the pattern.

By the method and system of the invention, the mathematical shape of the cornea is determined by assuming an analytical approximation to the surface shape. The analytical approximation is then substituted into a differential equation and some type of appropriate fit is performed to determine the coefficients that satisfy the differential equation. In a preferred embodiment of the invention, a nonlinear least squares fit is performed.

These operations are performed in the microprocessor 50. The processor has programming to review a great number of x values as determined on the detector 34, substituting all of these values into the differential equation and arriving at a formula for y and as a function of x.

A differential equation suitable for this purpose is $$dy/dx = -\left(\frac{a(y) - x}{b(y) - y}\right) \pm \left[\left(\frac{a(y) - x}{b(y) - y}\right)^2 + 1\right]^{\frac{1}{2}}.$$

where y is the depth of the reflection site away from a datum plane (such as the datum plane d shown in FIG. 1A), x is the distance from the visual axis, and a and b are coordinates representing the location of the real image of the illumination point in space. a is a distance of the particular illumination point 22a (see FIG. 1A) from the visual axis and b is the depth of that illumination point out from the datum plane d.

The differential equation used in this process is not new. It is a general equation which can be used to represent the shape of any surface, and is described in the article "Suggested New Methods for Photokeratoscopy, a Comparison for Their Validities, Part I", by S. G. El Hage, *American Journal of Optometry and Archives of American Academy of Optometry*, November 1971, page 897. In the article, El Hage discusses various uses of this general equation for solving the shape of the corneal surface. Also, he relates the corneal surface shape to one of the keratoscope rings in photokeratoscopy. Thus, this derivation in itself does not form a part of the present invention, but is hereby incorporated in this application by reference as illustrating that such derivation is known in the art.

At page 909, El Hage shows an optical arrangement for projecting an image onto a cornea and for detecting reflected light from the cornea. His source is analogous to the real image in the present invention, and El Hage had a number of optical elements between the source and the eye, including a beam splitter between the objective lens and the eye.

Returning to FIG. 1, the illuminating light source 12 may be a visible light source, in preferred embodiments of the invention wherein the system is not combined with a coaxial surgical laser. For example, an incandescent lamp can be used. The pattern plate or target 14 may be laser or photolithographically cut, with hole sizes on the range of about thirty microns. The beam splitter 16 may be a simple nondistorting plate glass beam splitter, with a surface coating of about 50% reflectivity.

Figure 1B:
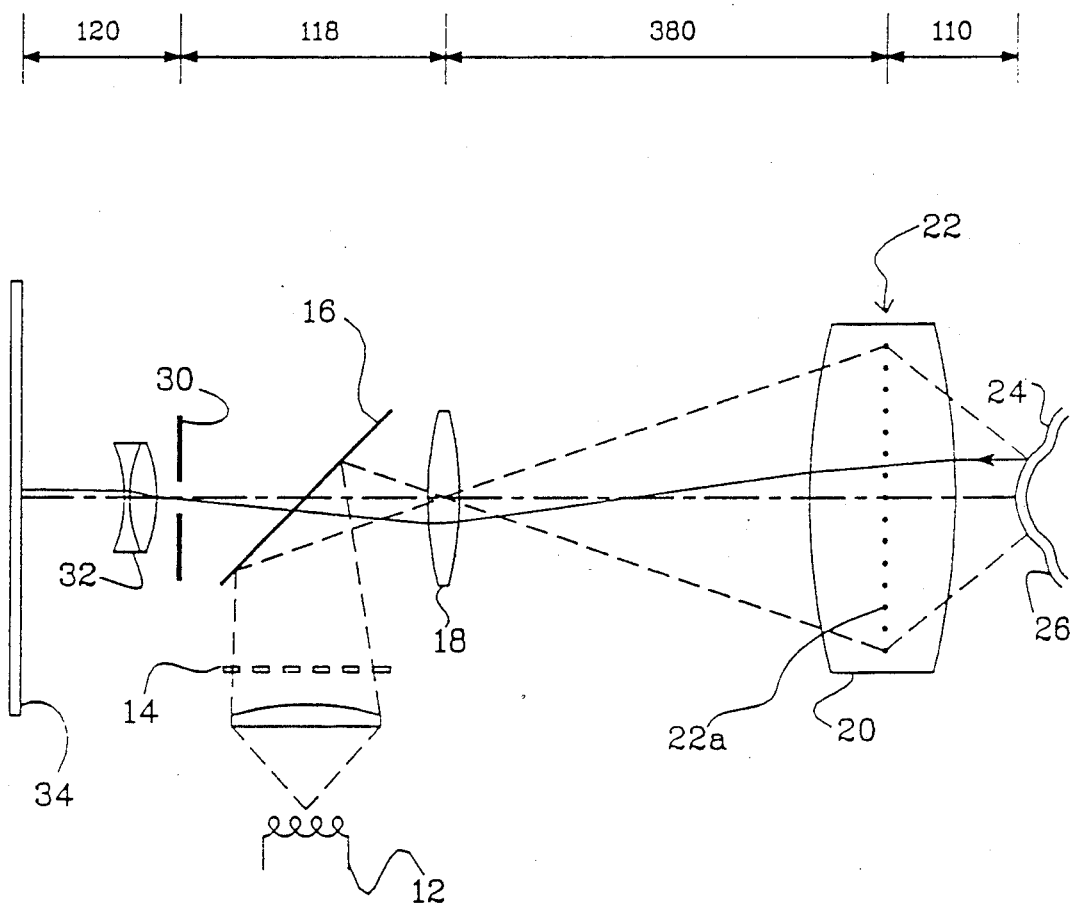
FIG. 1B is a view similar to FIG. 1, but showing a slightly modified form of the system, and with an example of distances and other optical values which can be used in the system.

In one specific embodiment of the invention, particular lenses and lens relationships may be selected as indicated in FIG. 1B. In FIG. 1B the distances between lenses, focal lengths and diameters of the various lenses are given for this specific embodiment. Other relationships and distances are also given, including the diameter of the aperture or spatial filter 30. The system of FIG. 1B shows a single light source 12 projecting a pattern and being folded into the optical axis of the instrument.

The detector or camera plane may comprise a high density photodetector array, for example.

Figures 3, 4:
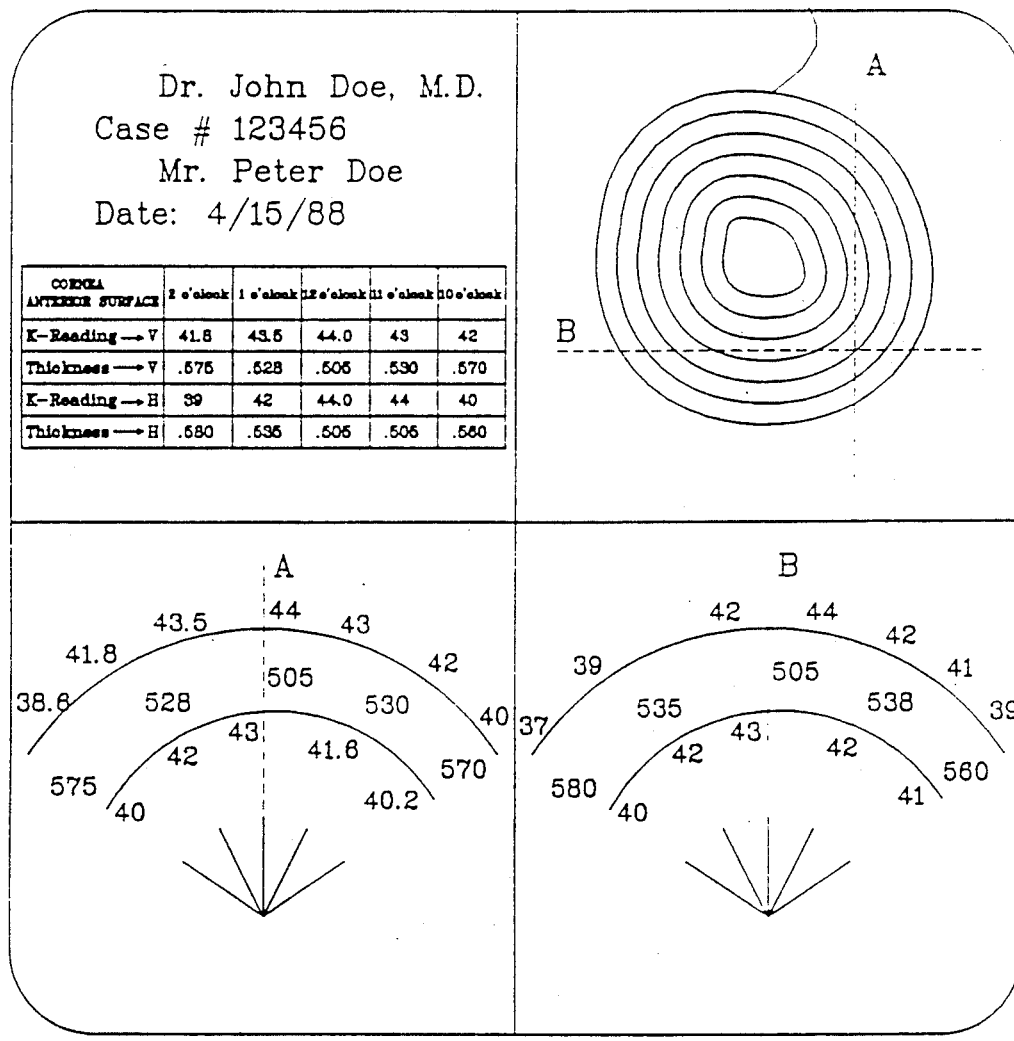
FIG. 3 is a schematic view showing an example of a video display which can be presented as a result of the information gathered by the instrument of the invention.
FIG. 4 is a view showing an example of quantitative information which can be displayed to the user of the instrument.

As indicated schematically in FIG. 1, the microprocessor 50 is connected to a display monitor 52. An example of the type of display that can be presented to the physician in real time is indicated in FIG. 3 by the reference number 54. In the upper left quadrant of the screen, patient identifying data is given, along with K-readings and thickness readings. A more detailed example of this information is shown in FIG. 4.

The lower left and lower right quadrants of the display 54 show examples of depth references of the epithelial and endothelial cornea surfaces at cutting planes A and B shown in the plan view of the upper right quadrant. The location of these cutting planes is preferably selectable by the physician, via inputs to the microprocessor 50 (not shown).

The distorted image 56 shown in the upper right quadrant of FIG. 3 is derived from a second projection which is preferably included in preferred embodiments of the invention. As illustrated in FIG. 1, a second projection may be folded onto the axis of the lens system via a second beam splitter 60, which reflects light from an illuminator light source 60 to a pattern or mask 64. The mask 64 has a plurality of concentric circle cuts so as to project a real image of the concentric circles in front of the cornea as is done with the pattern 22 of point light sources.

Figure 8:
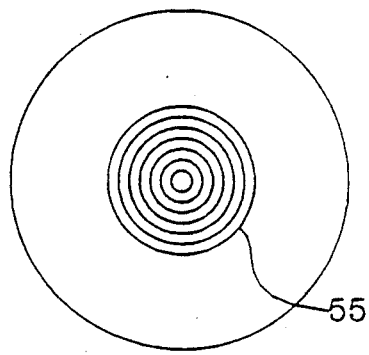
FIG. 8 is another schematic view showing concentric circles of light which can be projected on the cornea simultaneously with the pattern shown in FIG. 6 or FIG. 7, strictly for qualitative information for the surgeon, for comparing against the measurements determined from the quantitative measurements obtained via the pattern of FIG. 6 or FIG. 7.

FIG. 8 shows schematically a series of concentric circles in a pattern 55 which can be projected via the pattern plate 64. The detector 34, which may be a pixel array of very high density, can receive and detect both reflected images simultaneously. The concentric ring pattern can be discerned from the point source pattern by the contiguity of each ring. The software employed by the microprocessor 50 can sample each pixel receiving light and determine whether any immediately adjacent pixel is also receiving light. If so, the contiguity of a ring is indicated. In contrast, the patterns of point light sources such as shown in FIGS. 6 and 7 will not display appreciable contiguity. Thus, the microprocessor 50 can separate these images and analyze each separately. Alternatively, in a separate embodiment of the system and additional camera detector can be placed together with an additional beam splitter to separate the image of the continuous rings from the image of the discrete point sources.

As in a conventional corneoscope or in using a Placido ring, the concentric light rings produce a reflection off the cornea which is distorted in a way corresponding to distortions on the corneal surface. This can result, for example, in a pattern of distortion 56 such as shown in FIG. 3.

FIG. 1 shows that, with two different light patterns folded into the system, onto the axis of the lenses 18 and 20, polarizers 66 and 68 should be used to establish opposite polarity for the two different images being projected.

A polarizer used as an analyzer 94 may be rotated to select either of the projected images.

Figure 2:
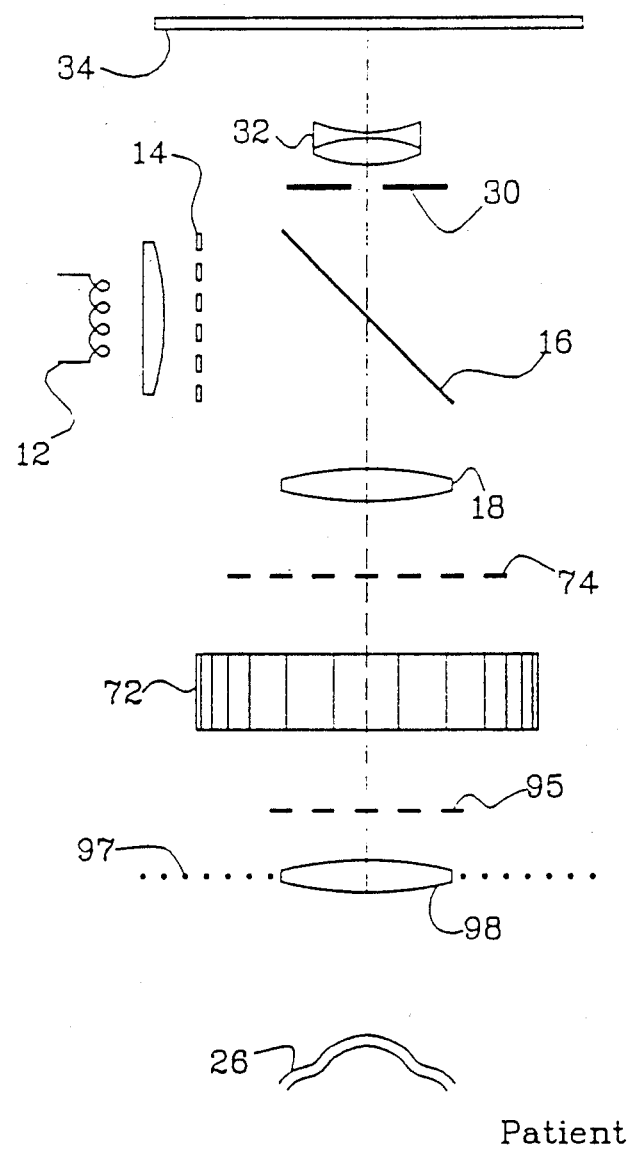
FIG. 2 is a schematic diagram showing portions of the apparatus of FIG. 1 as they can be incorporated into a surgical microscope, preferably with a simple auxiliary camera mount connection (for example, a C-mount connection).
Figure 5:
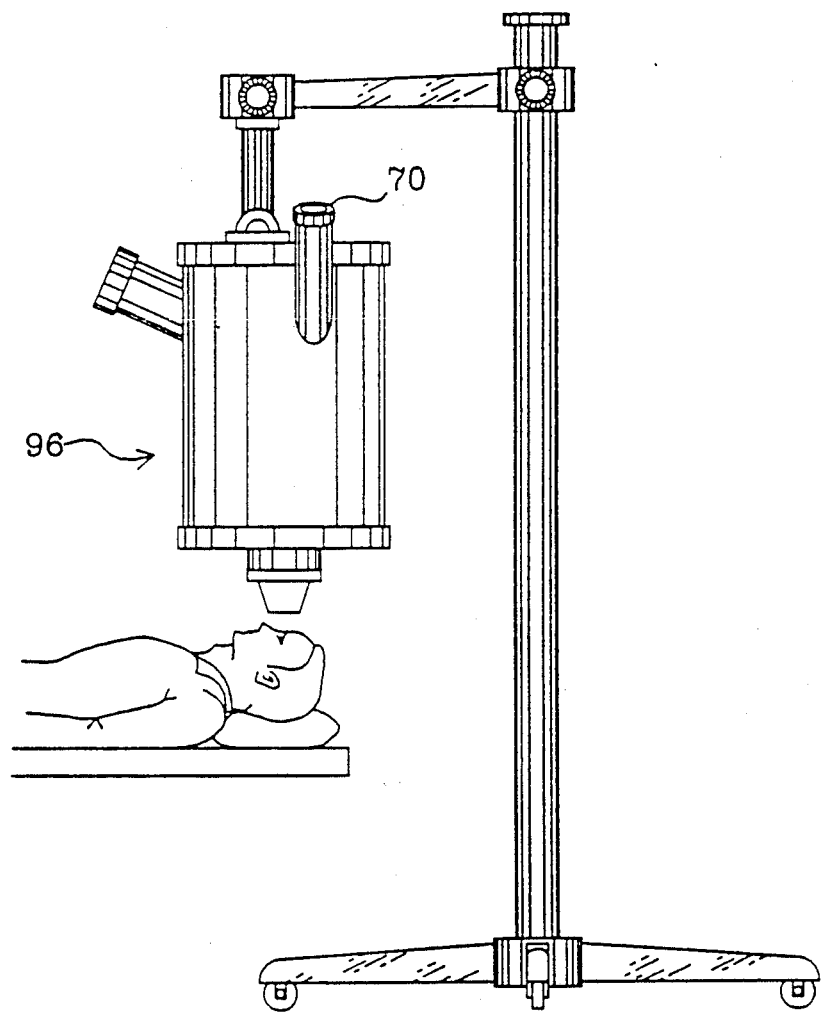
FIG. 5 is a view showing a conventional surgical microscope with which the embodiment of FIG. 2 can be used.

FIG. 2 is a schematic representation of an alternate embodiment showing some of the same elements present in the embodiment of FIG. 1, but in an arrangement for connection directly with a surgical microscope. Surgical microscopes, such as those made by Weck, Nikon, Topcon, Zeiss, Nidek, or Wild, usually include a standard auxiliary bayonet mount or screw attachment for a camera. FIG. 5 shows a typical standard surgical microscope. An auxiliary mount 70 (e.g. a C-mount) is shown in FIG. 5 and schematically indicated in FIG. 2 as coupling the system embodying the elements 12, 4, 34, 32, 18 and 16 to a fitting or optical tube 72 on the surgical microscope. Generally the surgical microscope will have optics to produce an image at an image plane 74 which is a standard distance from the auxiliary mount on the fitting 72, for coupling a standard 35 millimeter video camera to the surgical microscope. Thus, in this embodiment of the present invention, the objective lens 20 is eliminated and replaced by the objective lens 96 of the surgical microscope. The focal length of the lens 18 is adjusted to appropriately relay the Fourier plane 95 of the surgical microscope lens 96 to the aperture plane 30. In almost all other respects this embodiment is similar to the previously described embodiment. One possible exception is that if the F-number of the surgical microscope objective lens 96 is not sufficiently low to give the desired area of coverage on the cornea, then additional point sources 97 of light at multiple locations will be necessary outside the objective. These additional sources may be created with an illuminated pinhole mask or optical fibers.

Figure 11:
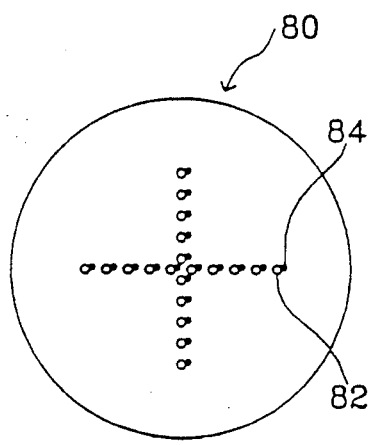
FIG. 11 is a schematic view showing a reflected pattern of discrete point light sources which might be received from the measurement projection shown in FIG. 6, and also showing an example of a secondary reflection which is taken from the endothelial surface, i.e. the back surface of the cornea.
Figure 12:
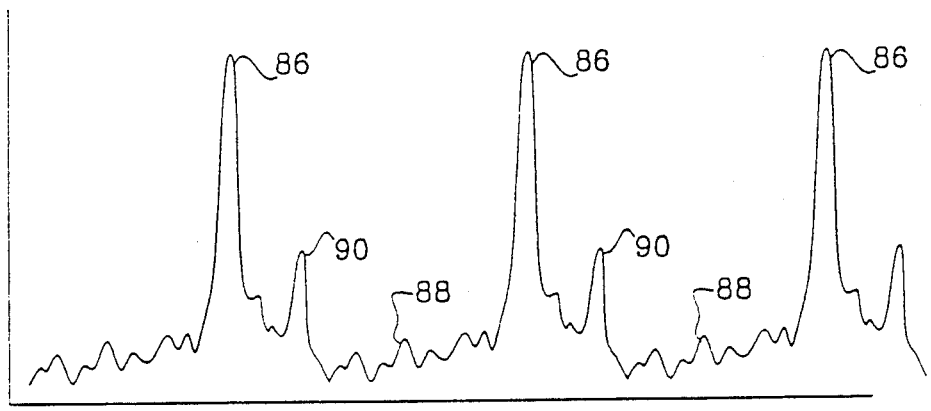
FIGS. 12, 13 and 14 are schematic graph plottings showing examples of light intensity versus distance across the cornea, for a reflected projection such as shown in FIG. 11, and indicating analysis of these reflections to obtain information as to both the front surface and the back surface of the cornea, i.e. the epithelial and endothelial surfaces.

FIGS. 11 through 14 illustrate an aspect of the system of the invention which enables both the epithelial corneal surface and the endothelial corneal surface to be detected and displayed in real time simultaneously. FIG. 11 shows an example of a reflected pattern 80 which might occur at the detector 34 from the simple pattern shown in FIG. 6 comprising a pair of orthogonal linear arrays of light points. As indicated in FIG. 11 each detected point 82 which is not on the optical axis will have a secondary reflection 84, of much lower intensity emanating from the back surface or endothelial surface of the cornea. The detected array might produce, for example, an intensity versus distance curve such as shown in FIG. 12. The long spikes 86 of light intensity represent the reflection of the discrete point light sources from the anterior, or front, surface of the cornea, with some degree of noise 88 occurring between the spikes. A secondary spike or cluster 90 of light intensity which is discernibly higher than the noise 88 occurs adjacent to each high intensity spike 86. This represents the lower-intensity reflection of the light points off the endothelial cornea surface. The plotting shown in FIG. 12 can easily be sampled or filtered to identify and separate the high intensity spikes 86 from the low intensity spikes 90. As can be appreciated by those skilled in this art, the programming in the computer can first determine the signal contribution from those spikes which achieve amplitudes above a predetermined threshold and then subtracting the contribution to the signal which correspond the high intensity spikes 86 to obtain a signal which contains only the low intensity spikes 90 and the noise 88. The process of identifying spike location for the high intensity spikes 86 is now repeated for the low intensity spikes 90, but with a lower threshold. In some embodiments of the invention, it may prove efficacious to electronically amplify the signal from which high intensity spikes 86 have previously been deducted in order to facilitate the threshold differentiation between low intensity spikes 90 from the noise 88. It is important to note that this selection process is facilitated by the observation that the specific amplitude of the spikes 86 and 90 are not as important as their actual location.

Figure 13:
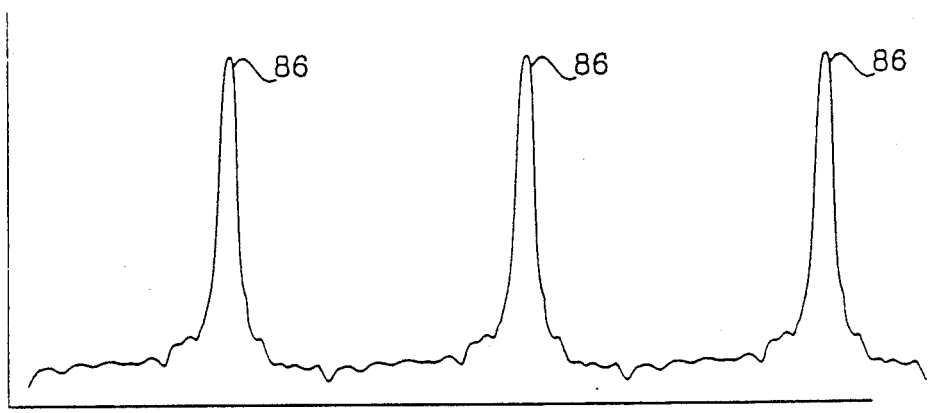
Figure 14:
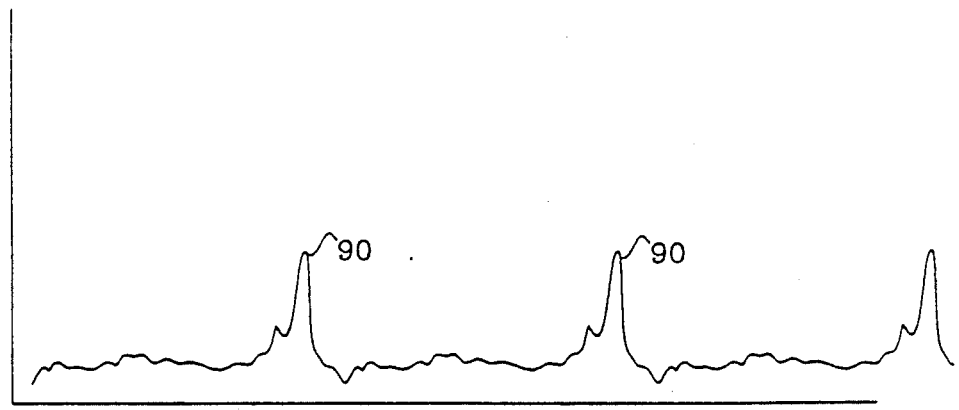

FIG. 13 and 14 show separate plottings of intensity versus distance for the front surface, anterior reflection and the rear surface, posterior reflection.

Once the primary and secondary reflections are known and located as in FIGS. 13 and 14, the shapes and elevation points of both the epithelial and endothelial surface can be calculated by the approximation method described previously, and two sets of data can thus be presented to the physician. Similarly, the cross sections and appropriate values can be represented in the lower two quadrants of the display as illustrated in FIG. 3.

It should be understood that in the drawings and the description herein, as well as in the claims, references to "up", "down", "lower", "upper", "left" or "right" are intended only for convenience in referring to the embodiments as represented in the drawings, and not as limiting any possible orientations of the instrument or components. The drawing figures are not to scale. Further, the term "objective lens" as used herein and in the claims and drawing figures is intended to refer to either an objective lens specific to the instrument or an objective or final focusing lens of a surgical microscope, if the instrument is used as part of a surgical microscope.

The above described preferred embodiments are intended to illustrate the principles of the invention, but not to limit its scope. Other embodiments and variations to these preferred embodiments will be apparent to those skilled in the art and may be made without departing from the spirit and scope of the invention as defined in the following claims.

We claim:

1. An ophthalmic diagnostic instrument for determining the shape of the cornea of a patient's eye, comprising,
   an objective lens as an optical element of the instrument, on an optical axis of the instrument,
   means for projecting a pattern of discrete separated point light sources and forming a real image of the pattern of point light sources at a position located between the interior of the objective lens and the patient's eye, the real image including point light sources in positions which traverse substantially directly across the optical axis,
   means for expanding the region of coverage on the cornea by using the objective lens as a field lens for the pattern image,
   means for selecting and collecting a reflected image of the pattern as reflected paraxially off the cornea, and for detecting a reflected position of substantially each point light source, as reflected from the cornea, including means for relaying the Fourier plane of the objective lens to a relayed position in the instrument, with aperture means positioned at said relayed position for limiting the collected light to that which is reflected paraxially off the cornea, whereby the aperture means is a spaced distance from the objective lens,
   means for analyzing the returned, collected pattern image and for comparing it to the undistorted pattern as projected, including analyzing the relative location and spatial orientation of the reflected point light sources as compared to the pattern as projected, and means for deriving mathematically a close approximation of a corneal surface shape that would give rise to such a collected pattern image, whereby the real image point sources, extending substantially across the optical axis, enable enhanced measurement of the central optical zone about the visual axis of the cornea.

2. Apparatus according to claim 1, wherein the pattern of discrete separated point light sources includes more than one rectilinear sequence.

3. Apparatus according to claim 1, wherein the pattern of discrete separated point light sources includes an asymmetrical shape having a plurality of lines of point light sources.

4. Apparatus according to claim 3, wherein the asymmetrical shape comprises generally a star with an odd number of points.

5. Apparatus according to claim 1, wherein the means for expanding the region of coverage comprises means for placing the source image in the objective lens, thus using it as a field lens.

6. Apparatus according to claim 1, in combination with a surgical microscope having a standard auxiliary camera mount, and the ophthalmic diagnostic instrument being connected to the surgical microscope via the auxiliary camera mount, with an objective lens of the surgical microscope serving as the objective lens of the ophthalmic diagnostic instrument.

7. Apparatus according to claim 1, including an illuminating light source, a pattern plate or mask positioned for projecting light from the light source through the plate, beam splitter means in the path of projected light from the pattern plate for reflecting and folding the projected pattern into a path coaxial with the optical axis of the instrument, with the beam splitter means located in said spaced distance between the aperture means and the objective lens, and optical means between the beam splitter means and the position of the patient's eye for focusing the projected pattern into the real image in front of the patient's eye.

8. Apparatus according to claim 7, further including means for receiving a reflected pattern from the cornea back through the optical means and through the beam splitter means, detector means on the opposite side of the beam splitter means from said optical elements, further optical means for focusing the return reflected and distorted pattern onto the detector means, and said aperture being positioned in a Fourier plane of the returning reflected pattern to eliminate substantially all light from the detector means except light reflected off the cornea as parallel to the optical axis of the instrument, whereby the spatial orientation of the pattern detected on the detector may be compared to the originally transmitted pattern for determination of the corneal shape through analysis of the positions of reflected points of the pattern.

9. Apparatus according to claim 1, wherein the ophthalmic diagnostic instrument includes means for folding the pattern of discrete separated point light sources onto the optical axis of the instrument, toward the cornea, with the means for projecting the pattern including a source of the pattern off-axis from the optical axis and from the path of the returned, distorted pattern image.

10. An ophthalmic diagnostic instrument for determining the shape of the cornea, comprising, an objective lens as an optical element of the instrument, on an optical axis of the instrument, means for projecting a pattern of discrete separated point light sources and forming a real image of the pattern of point light sources at a position located between the interior of the objective lens and the eye.

means for expanding the region of coverage on the cornea by using the objective lens as a field lens for the pattern image, means for selecting and collecting a reflected image of the pattern as reflected paraxially off the cornea, and for detecting a reflected position of substantially each point light source, as reflected from the cornea, including means for relaying the Fourier plane of the objective lens to a relayed position in the instrument, with aperture means positioned at said relayed position for limiting the collected light to that which is reflected paraxially off the cornea, whereby the aperture means is a spaced distance from the objective lens, means for analyzing the returned, collected pattern image and for comparing it to the undistorted pattern as projected, including analyzing the relative location and spatial orientation of the reflected point light sources as compared to the pattern as projected, means for deriving mathematically a close approximation of a corneal surface shape that would give rise to such a collected pattern image, and means for projecting a second light pattern comprising concentric circles toward the cornea simultaneously with said pattern of discrete separated point light sources, and means for separately analyzing distorted reflected light from the cornea relating to the concentric circles and for providing separate, qualitative information which can be compared with the corneal surface shape derived via the pattern of discrete separated point light sources.

11. Apparatus according to claim 10, wherein said means for projecting a second light pattern includes a second light pattern illuminating source, a second pattern plate or mask, second beam splitter means positioned along the axis of the instrument and in position to fold a projected pattern from the second pattern mask onto the optical axis of the instrument, and a first polarizer in the path of the projected pattern of discrete separated point light sources and a second polarizer in the path of the second light pattern, with opposite polarity established by the orientation of the two polarizers such that the two projected patterns are projected to real image locations with opposite polarity, and such that their reflections are more easily separable with a polarizing analyzer at the detector means.

12. Apparatus according to claim 1, further including means for separately analyzing a secondary returned, reflected pattern image as reflected from the back or endothelial surface of the cornea.

13. Apparatus according to claim 12, wherein said means for separately analyzing includes filtering means for electronically separating returned light points on the detector means occurring from the front surface of the cornea from those occurring from the back surface of the cornea, by separating different ranges of amplitude of the detected light.

14. Apparatus according to claim 13, wherein said means for deriving mathematically includes computer means for determining the endothelial corneal surface shape from the locations on the detector means of the detected light points reflected from the endothelial surface.

15. Apparatus according to claim 1, wherein the means for projecting a pattern includes an illuminating light source and a plate with a laser-cut or photolithographically produced pattern of discrete holes to form the discrete separated point light sources.

16. An ophthalmic diagnostic instrument for determining the shape of the cornea, comprising, an objective lens as an optical element of the instrument, on an optical axis of the instrument, means for projecting a pattern of discrete separated point light sources and forming a real image of the pattern of point light sources at a position located between the interior of the objective lens and the eye, means for expanding the region of coverage on the cornea by using the objective lens as a field lens for the pattern image, means for selecting and collecting a reflected image of the pattern as reflected paraxially off the cornea, and for detecting a reflected position of substantially each point light source, as reflected from the cornea, including means for relaying the Fourier plane of the objective lens to a relayed position in the instrument, with aperture means positioned at said relayed position for limiting the collected light to that which is reflected paraxially off the cornea, whereby the aperture means is a spaced distance from the objective lens, means for analyzing the returned, collected pattern image and for comparing it to the undistorted pattern as projected, including analyzing the relative location and spatial orientation of the reflected point light sources as compared to the pattern as projected, means for deriving mathematically a close approximation of a corneal surface shape that would give rise to such a collected pattern image, including means for utilizing the detected spatial orientation of the reflected point light sources to determine the corneal shape along a selected cutting plane on the eye in accordance with the general formula $$dy/dx = -\left(\frac{a(y)-x}{b(y)-y}\right) \pm \left[\left(\frac{a(y)-x}{b(y)-y}\right)^2 + 1\right]^{\frac{1}{2}}.$$

whereby y is depth of a cornea reflection point from a datum plane, x is distance from the optical axis of the instrument, and (a, b) are the coordinates of the real image of an illumination point space.

17. A method for determining the shape of the cornea of an eye, comprising, projecting a pattern of discrete separated point light sources and forming a real image of the pattern of point light sources at a position located in front of the eye, the real image including point light sources in positions which traverse substantially directly across the visual axis of the eye, selecting and collecting a reflected image of the pattern as reflected paraxially off the cornea, and detecting a reflected position of substantially each point light source, as reflected from the cornea, analyzing the returned, collected pattern image for comparing it to the undistorted pattern as projected, including analyzing the relative location and spatial orientation of the reflected point light sources as compared to the pattern as projected, and deriving mathematically a close approximation of a corneal surface shape that would give rise to such a collected pattern image. An ophthalmic diagnostic instrument for determining the shape of the cornea, comprising, an objective lens as an optical element of the instrument, on an optical axis of the instrument, means for projecting a pattern of discrete separated point light sources and forming a real image of the pattern of point light sources at a position located between the interior of the objective lens and the eye, means for expanding the region of coverage on the cornea by using the objective lens as a field lens for the pattern image, means for selecting and collecting a reflected image of the pattern as reflected paraxially off the cornea, and for detecting a reflected position of substantially each point light source, as reflected from the cornea, including means for relaying the Fourier plane of the objective lens to a relayed position in the instrument, with aperture means positioned at said relayed position for limiting the collected light to that which is reflected paraxially off the cornea, whereby the aperture means is a spaced distance from the objective lens, means for analyzing the returned, collected pattern image and for comparing it to the undistorted pattern as projected, including analyzing the relative location and spatial orientation of the reflected point light sources as compared to the pattern as projected, means for deriving mathematically a close approximation of a corneal surface shape that would give rise to such a collected pattern image, and whereby the real image point sources, extending substantially across the optical axis, enable enhanced measurement of the central optical zone about the visual axis of the cornea.

18. The method of claim 17, wherein the pattern of discrete separated point light sources comprises a generally cruciform shaped pattern with crossing rectilinear rays of point light sources as an intersection point lying on the optical axis of the instrument.

19. The method of claim 17, wherein the pattern of discrete separated point light sources comprises a generally asterisk shaped pattern with an intersection point at the optical axis of the instrument, and including means associated with the pattern for establishing a readily identifiable rotational orientation of the pattern.

20. The method of claim 17, including using an off-axis illuminating light source and projecting light through a pattern mask and then reflecting the projected pattern off a beam splitter to fold the projected pattern into a path coaxial with the optical axis of the instrument, focusing the projected pattern reflected off the beam splitter to form the real image in front of the patient's eye, receiving a reflected pattern from the cornea back through the beam splitter and focusing the reflected pattern onto the detector, and including passing the returning reflected light pattern through an aperture en route to the detector to eliminate all light reflected off the cornea except that which is parallel to the optical axis of the instrument, whereby the spatial orientation of the pattern detected on the detector may be compared to the originally transmitted pattern for determination of the corneal shape through analysis of the positions of reflected points of the pattern.

21. A method for determining the shape of the cornea of an eye, comprising, projecting a pattern of discrete separated point light sources and forming a real image of the pattern of point light sources at a position located in front of the eye, selecting and collecting a reflected image of the pattern as reflected paraxially off the cornea, and detecting a reflected position of substantially each point light source, as reflected from the cornea, analyzing the returned, collected pattern image for comparing it to the undistorted pattern as projected, including analyzing the relative location and spatial orientation of the reflected point light sources as compared to the pattern as projected, deriving mathematically a close approximation of a corneal surface shape that would give rise to such a collected pattern image, and projecting a second light pattern comprising concentric circles toward the cornea simultaneously with the pattern of discrete separated point light sources, and separately analyzing reflected light from the cornea relating to concentric circles and providing separate, qualitative information which can be compared with the corneal surface shape derived via the pattern of discrete separated point light sources.

22. The method of claim 17, further including separately analyzing a secondary returned, reflected pattern image as reflected from the back or endothelial surface of the cornea.

23. The method of claim 22, wherein the step of separately analyzing includes electronically separating returned light point on the detector means occurring from the front surface of the cornea from those occurring from the back surface of the cornea, by separating different ranges of amplitude of the detected light on the detector.

24. The method of claim 23, including mathematically deriving the endothelial corneal surface shape on a computer, from the locations on the detector of the detected light points reflected from the endothelial surface.

25. A method for determining the shape of the cornea of an eye, comprising, projecting a pattern of discrete separated point light sources and forming a real image of the pattern of point light sources at a position located in front of the eye, selecting and collecting a reflected image of the pattern as reflected paraxially off the cornea, and detecting a reflected position of substantially each point light source, as reflected from the cornea, analyzing the returned, collected pattern image for comparing it to the undistorted pattern as projected, including analyzing the relative location and spatial orientation of the reflected point light sources as compared to the pattern as projected, and deriving mathematically a close approximation of a corneal surface shape that would give rise to such a collected pattern image, including utilizing the detected spatial orientation of the reflected point light sources to determine the corneal shape along a selected cutting plane on the eye in accordance with the general formula $$dy/dx = -\left(\frac{a(y) - x}{b(y) - y}\right) \pm \left[\left(\frac{a(y) - x}{b(y) - y}\right)^2 + 1\right]^{\frac{1}{2}}.$$

where y is depth of a cornea reflection point from a datum plane, x is distance from the optical axis of the instrument, and (a, b) is the coordinate location of the real image of an illumination point in space.

26. The method of claim 17, further including electronically producing cross sectional images of the eye at selected cutting planes using information derived from the mathematical derivation of the corneal surface shape.

27. The method of claim 17, wherein the pattern of discrete separated point light sources is projected through the objective lens of a surgical microscope, and including collecting the returned pattern image through the objective lens of the surgical microscope.

28. The method of claim 21, further including producing and displaying an image showing the distortion of the projected concentric circles.

29. The method of claim 17, wherein a front objective lens comprises an element closest to the eye of the patient, and including spacing the front objective lens at least about 110 mm away from the eye.

30. The method according to claim 17, including forming the real image of the pattern of point light sources substantially in the objective lens, so as to use the objective lens as a field lens, enabling a larger field of view of the cornea.

* * * * *